United States Patent [19]
Nowicky

[11] Patent Number: 5,888,991
[45] Date of Patent: Mar. 30, 1999

[54] USE OF PHOSPHORUS DERIVATIVES OF ALKALOIDS FOR TREATING ENDOCRINOPATHIES

[76] Inventor: Wassyl Nowicky, 7 Margaretenstrasse, A-1040 Vienna, Austria

[21] Appl. No.: 669,409
[22] PCT Filed: Mar. 20, 1995
[86] PCT No.: PCT/AT95/00055
 § 371 Date: Jul. 9, 1996
 § 102(e) Date: Jul. 9, 1996
[87] PCT Pub. No.: WO95/25522
 PCT Pub. Date: Sep. 28, 1995

[30] Foreign Application Priority Data

Mar. 18, 1994 [AT] Austria ................................. 578/94

[51] Int. Cl.[6] .................. A61K 31/675; A61K 31/66
[52] U.S. Cl. ....................... 514/81; 514/142; 514/144
[58] Field of Search ..................... 514/101, 81, 142, 514/144

[56] References Cited

U.S. PATENT DOCUMENTS 4,816,462 3/1989 Nowicky ................................ 514/279

FOREIGN PATENT DOCUMENTS 354644 1/1980 Austria .
377988 5/1985 Austria .
326627 8/1989 European Pat. Off. .

OTHER PUBLICATIONS

Kleinrok, Z., et al. 'Some Pharmacological Properties . . . ' Drugs Under Experimental and Clinical Research, vol. 18, 1992 pp. 93–96.

Jagiello–Wojtowicz, E., et al. 'Effect of Single . . . ' Drugs Under Experimental and Clinical Research, vol. 18, 1992, pp. 85–87.

Jagiello–Wojtowicz, E., et al., 'Effect of Prolonged . . . ' Drugs Under Experimental and Clinical Research, vol. 18, 1992, pp. 89–91.

Jagiello–Wojtowicz, E., et al. "Effect of Three Months Treatment with Ukrain on Peripheral Blood Morphology in Rodents." Drugs Exptl. Clin. Res. Supplement to Vol. XVIII, (1992) pp. 79–83.

Chem. Abstr. 105, 60 797 M 1986, Nowicky et al.

S. Simeon et al., Pharmazie 44 (1989) H.9, pp. 593–597.

Hagers Handbuch der pharmazeutischen Praxis, 4 ed., Springer–Verlag, Berlin–Heidelberg–New York, vol. 3, (1972/pp. 835–841).

*Primary Examiner*—Theodore J. Criares
*Attorney, Agent, or Firm*—Ladas & Parry

[57] ABSTRACT

The invention concerns the use of phosphorus derivatives of alkaloids of the general formula (I), for preparing a medicament for treating endocrinopathies, in particular for treating osteoporosis.

3 Claims, No Drawings

USE OF PHOSPHORUS DERIVATIVES OF ALKALOIDS FOR TREATING ENDOCRINOPATHIES

This application is a 371 of PCT/AT95/00055 filed Mar. 20, 1995.

The present invention relates to the use of phosphorus derivatives of alkaloids for producing a medicament for treating endocrinopathies.

The term endocrinopathies indicates syndromes in which dyshormonisms are the main cause and determinative of the disease. The causes of such syndromes may reside in diseases of the endocrinal glands, e.g. in an increased hormone production or in a hormome hunger or in a complete absence of hormones, in dysfunctions of the endocrinal glands due to regulatory processes, in derailed hormone formation as a consequence of pathological enzyme systems or in a changed responsiveness of various organs to hormones.

Osteoporosis also can be counted among the endocrinopathies, this being the quantitative reduction of the bone tissue with a retained bone structure due to an increased bone degradation and/or a reduced bone

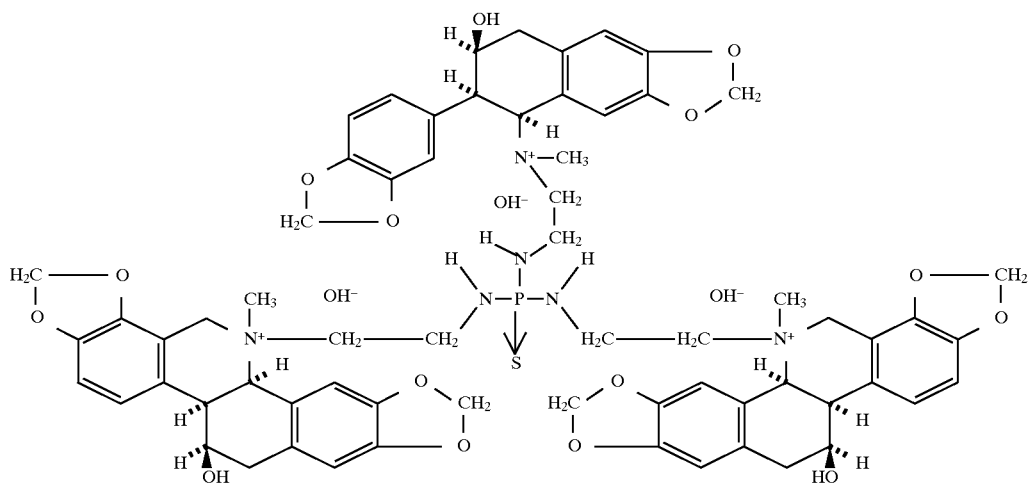

formation, accompanied by the increased occurrence of heparin-containing mast cells in the bone marrow. The etiology of this disease is largely unclear, yet there are strong hints indicating that it is at least very much encouraged by an estrogen deficiency due to the incidence of menopause.

An article by H. Resch et al. (Calcif. Tissue Int. (1989) 45:209–213) proposes the combined administration of calcitonin and a cyclical hormone replacement therapy for the treatment of osteoporosis. Furthermore, in Acta Endocrinologica 1990, 123, p. 14–18, the same author has described the cyclical estrogen/progestogen replacement therapies for treating osteoporosis. The results of these studies indicate that hormone treatment of patients suffering from osteoporosis seems to be promising.

In Osteoporosis, Wilhelm Maudrich Publishers, Wien-München-Bern, 1989, B.E.C. Nordin also argues that at least in women the increased bone resorption involved with osteoporosis presumably goes back to a decreasing functioning of the ovaries, the androstenedione produced by the suprarenal cortex being the only estrogen source after menopause, from which in turn only slight amounts of estradiole are being produced. A small amount of estradiol is formed by the peripheral conversion from testosteron, which in turn is partly formed from the androstenedione of the suprarenal cortex and partly is formed in the post-menopausal ovary. In view of this rather complex mechanism, it is hard to say which hormonal changes are responsible for the increasing bone resorption in menopause. Since the latter is reversible by an estrogen therapy, it is probably due to the decrease of the entire effective estrogen activity (estradiol and estrone). However, the ovary insufficiency need not necessarily have a direct effect on the bones; indirectly it would act via changes in the calcitonin secretion. In the direct post-menopausal phase, the serum calcium and the urine calcium certainly will increase without an increase in the calcium resorption, and in this case the calcium demand may even rise to up to 35 mmol/day. As regards the effects of various hormones or the deficiencies thereof, respectively, on osteoporosis, reference is made to the last-mentioned publication by B.E.C. Nordin.

AT PS 377 988 and AT PS 354 644 disclose methods of producing novel phosphorus derivatives of alkaloides and novel salts of alkaloid derivatives of thiophosphoric acid, respectively. Such compounds have a pharmacological activity and may be used as cytostatic agents. Compound is disclosed in AT 377988 in Example 1.

Surprisingly it has now been found that the phosphorus derivatives of alkaloids disclosed in AT PS 377 988 and AT PS 354 644, respectively, can be used for the production of medicaments for the treatment of endocrinopathies, in particular for the treatment of osteoporosis.

Methods of producing phosphorus derivatives of alkaloids of the general formula (I)

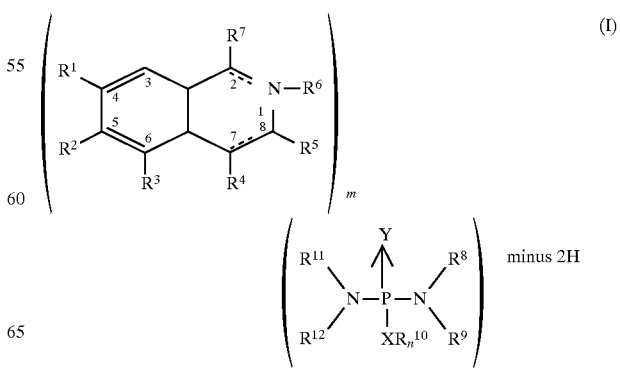

wherein m and n=1, 2 or 3; $R^1$, $R^2$ and $R^3$ are each independently H or methoxy, wherein $R^1$ and $R^2$ or $R^2$ and $R^3$ together also can represent a methylene dioxy group;

$R^4$ and $R^5$ together with the C atoms to which they are attached form a possibly totally or partially hydrogenated phenyl or naphthyl group which in turn may be substituted by methoxy, hydroxy or dioxymethyl, wherein $R^7$ is H or =O or an equal ring system bonded via a —$CH_2$—CO—$CH_2$- chain, $R^6$ is —$CH_3$ and double bonds may be present in positions 1, 2 and/or 7, 8; or $R^6$ and $R^7$ together with the C and N atoms to which they are attached form a possibly hydrogenated benzo or naphtho ring system, which in turn may be substituted by methoxy, oxo, methyl or dioxymethyl groups, wherein the C—N bond in positions 1, 2 may be missing and $R^4$ and $R^5$ are H;

$R^{10}$=2H, —$CH_2$—$CH_2$—, H or —$CH_2$—$CH_2$Cl;

$R^8+R^9$ and $R^{11}+R^{12}$ are —$CH_2$—$CH_2$— and, if Y=S, X=N and n=2, $R^2$ and $R^3$ are —$CH_2$—$CH_2$—, —$CH_2$—$CH_2$—O—$CH_2$—$CH_2$— or

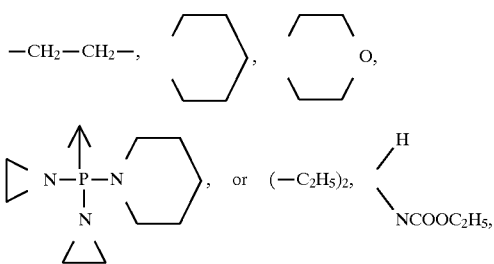

if

Y=S, X=N, n=2, $R^2$ and $R^3$ represent

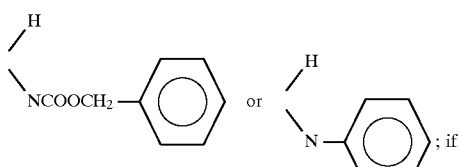

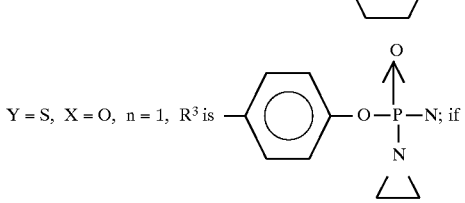

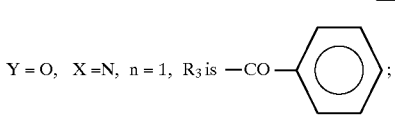

-continued

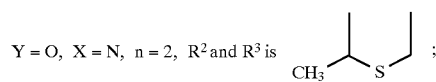

and, if

Y=O, X=O, n=1, $R^8$ and $R^9$ are each —$CH_2$—$CH_2$—Cl, $R^{10}$ is $H_2$ and $R^{11}+R^{12}$ are —$CH_2$—$CH_2$— or —$CH_2$—$CH_2$—$CH_2$—, if Y=S, X=N, $R^3$ is —$CH_2$—$CH_2$—, as well as the salts thereof with pharmaceutically compatible acids, are known from AT PS 377 988; the preparation of alkaloid derivatives of thiophosphoric acid of the general formula

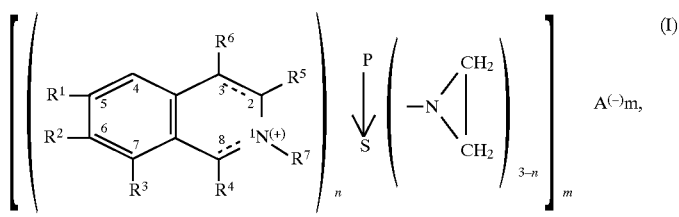

wherein n is 1, 2 or 3; m is 1, 2 or 3; $R^1$, $R^2$ and $R^3$ independently each are hydrogen or methoxy, wherein $R^1$ and $R^2$ or $R^2$ and $R^3$ together also may represent a methylene-dioxy group; $R^4$ is hydrogen, hydroxy or methyl; and, if $R^6$ is hydrogen, $R^5$ and $R^7$ together form the group

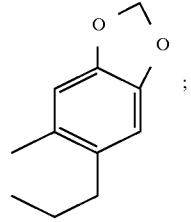

or, if $R^7$ is a methyl group, the groups $R^5$ and $R^6$ represent the group

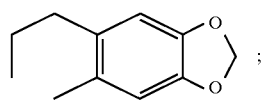

and in positions 1, 8 and/or 2, 3 a double bond may be present; and A is a monovalent or the equivalent portion of a polyvalent anion, is disclosed in AT PS 354 644.

According to a particularly preferred embodiment of the present invention, the reaction product of the alkaloids of chelidonium majus L. with thiophosphoric acid triaziridide is used for the production of a medicament for the treatment of endocrinopathies, in particular for the treatment of osteoporosis. For reasons of simplicity, this reaction product will be termed "ukrain" in the following.

The surprising effect of ukrain in the treatment of endocrinopathies shall be demonstrated in the following by way of an animal test model.

Therein, the sustained action of ukrain on some biochemical and biomechanical parameter is investigated in ovariectomized rats.

Ovariectomy is an acknowledged model for the experimental osteoporosis. The test animals received intraperitoneal injections of ukrain at a dose of 28 mg/kg body weight per day for 6 months, starting from the second day after the removal of the ovaries or after corresponding surgery without removal of the ovaries (control group with surgical shock). Ovariectomy caused changes in the peripheral blood morphology, the activity of amino transferases (ALT and AST) and in the total serum protein level as well as in the serum hormone concentrations and in the amount of catecholamines in the complete brains of the rats. The changes are given in detail in the following tables.

TABLE I

Effects of the 6-month treatment with ukrain on the levels of some hormones in the sera of ovariectomized rats (N = 10)

| Treatment | Prolactin ng/ml | Progesterone ng/ml | ACTH pg/ml | Corticosterone ng/ml | Aldosterone pg/ml | T-3 ng/ml | T-4 ng/ml | $T_3$-Uptake |
|---|---|---|---|---|---|---|---|---|
| Control group | 18.5 ± 0.02 | 12.9 ± 2.9 | 115.6 ± 26.36 | 470 ± 79.7 | 227.14 ± 30.5 | 0.82 ± 0.07 | 140.8 ± 5.2 | 1.7 ± 1.09 |
| Control group with surgical shock | 10.5 ± 0.15 | 17.9 ± 5.8 | 167.85 ± 66.25 | 513.12 ± 112.2 | 361.2 ± 89.2 | 0.72 ± 0.14 | 141.2 ± 9.3 | 41.4 ± 0.98 |
| Ovariectomized control group | 9.3 ± 0.16 | 5.56 ± 1.38 | 99.37 ± 21.2 | 434.0 ± 83.9 | 246 ± 40.9 | 0.52 ± 0.036 | 140.5 ± 6.3 | 41.98 ± 0.41 |
| Ovariectomy, treatment with ukrain 28 mg/kg body weight i.p. | 11.9 ± 0.01 | 20.9 ± 0.49 | 114.6 ± 20.9 | 243.7 ± 46.1 | 97.8 ± 30.9 | 0.49 ± 0.03 | 130.4 ± 9.7 | 41.37 ± 0.67 |

T3 = Triiodothyroidine
T4 = Thyroxine

TABLE II

Effects of the 6-month-treatment with ukrain on the amounts of noradrenaline (NA) and dopamine (DA) in the complete brains in ovariectomized rats (N = 10)

| | ng/g Fresh Tissue | |
|---|---|---|
| Treatment | NA | DA |
| Control group | 1.214 ± 0.043 | 0.778 ± 0.032 |
| Control group with surgical shock | 1.4703 ± 0.077 | 0.913 ± 0.061 |
| Ovariectomized control group | 1.625 ± 0.064 | 1.0208 ± 0.047 |
| Ovariectomy, treatment with ukrain 28 mg/kg body weight, i.p. | 1.274 ± 0.085 | 0.920 ± 0.027 |

TABLE III

Effects of the 6-month-treatment with ukrain on the activities of aminotransferases (ALT and AST) in the sera of ovariectomized rats (N = 10)

| | Activity, i.p. | |
|---|---|---|
| Treatment | ALT | AST |
| Control group | 25.3 ± 0.4 | 19 ± 0.6 |
| Control group with surgical shock | 25.8 ± 0.4 | 23.5 ± 0.5 |
| Ovariectomized control group | 25.1 ± 0.6 | 21.3 ± 0.3 |

TABLE III-continued

Effects of the 6-month-treatment with ukrain on the activities of aminotransferases (ALT and AST) in the sera of ovariectomized rats (N = 10)

| | Activity, i.p. | |
|---|---|---|
| Treatment | ALT | AST |
| Ovariectomy, treatment with ukrain 28 mg/kg body weight, i.p. | 24 ± 0.4 | 19.4 ± 0.5 |

TABLE IV

Effects of 6-month-treatment with ukrain on the peripheral blood morphologies in overiectomized rats (N = 10)

| Treatment | Hemoglobin g % | Erythrocytes $10^6/mm^3$ | Haematocrit % | Leucocytes $10^3/mm^3$ |
|---|---|---|---|---|
| Control Group | 144 ± 0.14 | 7.5 ± 0.08 | 40.8 ± 0.3 | 14.4 ± 0.14 |
| Control group with surgical shock | 15.5 ± 0.2 | 8.18 ± 0.06 | 45.6 ± 0.17 | 15.5 ± 0.2 |

TABLE IV-continued

Effects of 6-month-treatment with ukrain on the peripheral blood morphologies in overiectomized rats (N = 10)

| Treatment | Hemoglobin g % | Erythrocytes $10^6/mm^3$ | Haematocrit % | Leucocytes $10^3/mm^3$ |
|---|---|---|---|---|
| Ovariectomized control group | 15.5 ± 0.3 | 8.05 ± 0.02 | 44.9 ± 0.04 | 15.5 ± 0.3 |
| Ovariectomy, treatment with ukrain 28 mg/kg body weight i.p. | 14.8 ± 0.07 | 7.9 ± 0.03 | 43.2 ± 0.2 | 14.8 ± 0.07 |

From the above Tables I to IV it is apparent that the changes caused by ukrain in ovariectomized rats is significant insofar as all the parameters which are out of the ordinary after an ovariectomy and thus, most likely, also in case of osteoporosis, are improved.

In this context it is also particularly remarkable that after the treatment and sacrifice of the animals a significantly better mechanical breaking loadability of the femora resulted in animals treated with ukrain as compared to the ovariectomized control group.

As the alkaloid component, the following have proved particularly suitable: Coptisin, stylopin, berberin, protopin allo-cryptopin, spartein, corysamin, chelidimerin, oxysanguinarin, sanguinarin, dihydroxysanguinarin, chelidonin, homochelidonin, methoxy-chelidonin, chelerythrin, chelilutin, winblastin, colchicin, cholchicein, desacetyl-N-methyl-colchicin.

As the phosphorus compound for the reaction, the following are particularly suitable:

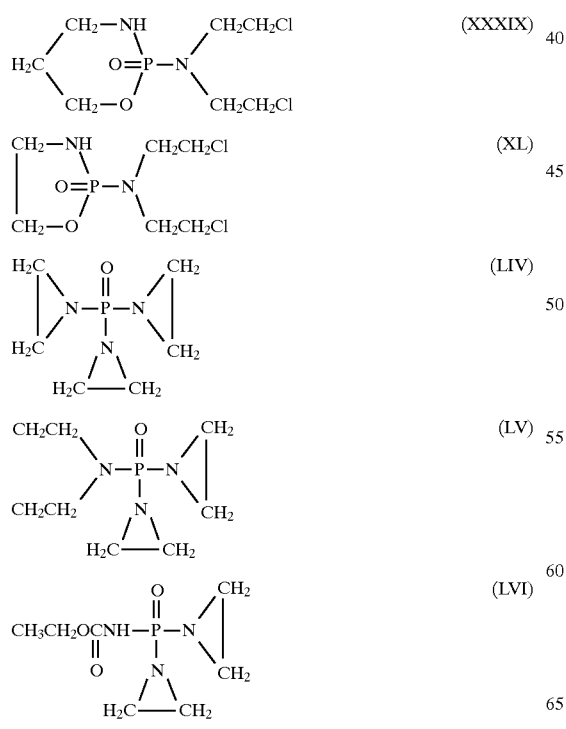
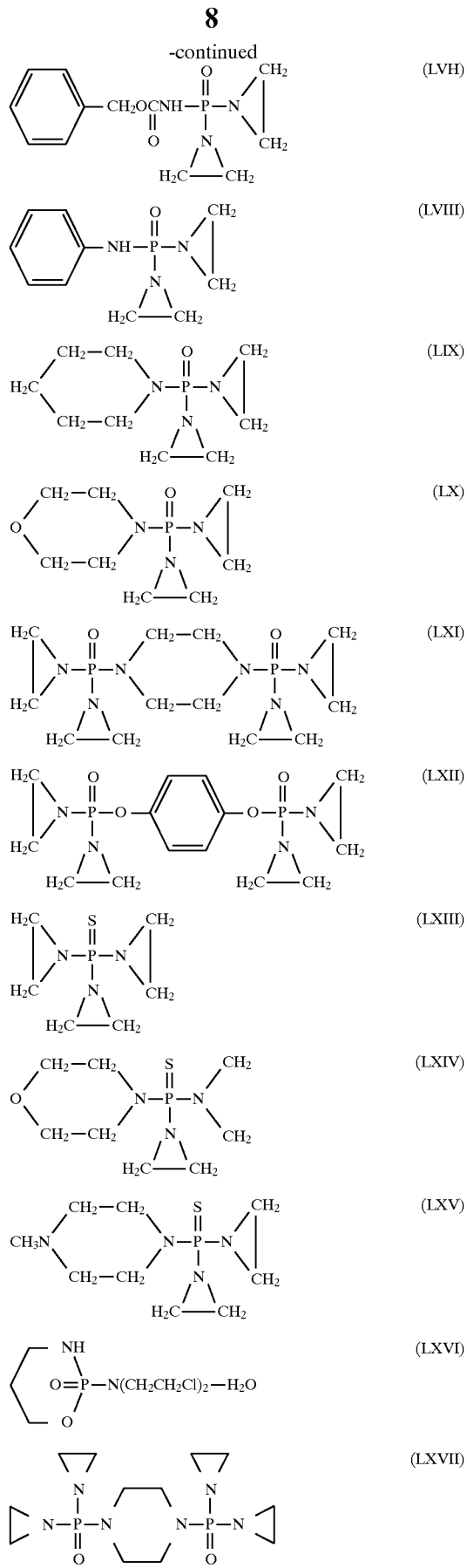

-continued

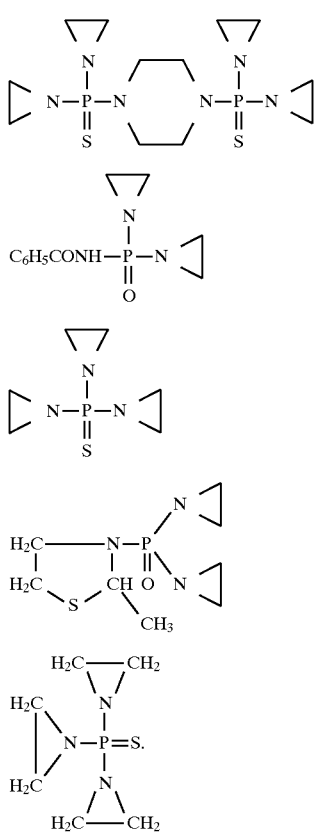

(LXVIII)
(LXIX)
(LXX)
(LXXI)
(LXXII)

The medicaments produced according to the invention preferably are comprised of an aqueous solution of the alkaloid phosphorus derivatives used or of the salts thereof, possibly in combination with further auxiliary agents known per se. The medicament according to the invention preferably is administered by way of injection, e.g. intraperitoneally, intramuscularly or intravenously, the dosage being dependent on the respective case and on the severity of the disease to be treated as well as on the condition of the patient.

It is within the knowledge of the medical doctor in charge to determine the suitable dosage in each case.

I claim:

1. A method for treating osteoporosis comprising administering to a patient in need of such treatment a phosphorus derivative of alkaloids of formula (I), salts or pharmaceutically compatible acids, thereof $$\left( \begin{array}{c} R^1 \\ R^2 \\ R^3 \end{array} \begin{array}{c} R^7 \\ \\ R^4 \end{array} N-R^6 \atop R^5 \right)_m \quad (I)$$

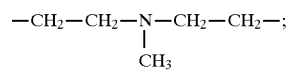
minus 2H wherein m and n=1, 2 or 3; $R^1$, $R^2$ and $R^3$ are independent and each represent H or methoxy, or $R^1$ and $R^2$ or $R^2$ and $R^3$ together also may represent a methylene dioxy group;

$R^4$ and $R^5$ together with C atoms to which they are attached can be a phenyl or naphthyl group, which is not hydrogenated, partially hydrogenated or totally hydrogenated, which may be substituted by methoxy, hydroxy or dioxymethyl; $R^7$ is H or =O or a ring system defined above bonded via a —CH$_2$—CO—CH$_2$— chain; $R^6$ is —CH$_3$ and double bonds may be present in positions 1, 2 and/or 7, 8; or $R^6$ and $R^7$ together with the N and C atoms to which they are attached form a possibly hydrogenated benzo or naptho ring system which may be substituted by methoxy, oxo, methyl or dioxy-methyl groups, wherein the C—N bond in positions 1, 2 may be missing and $R^4$ and $R^5$ represent H;

$R^{10}$=H$_2$, —CH$_2$—CH$_2$—, —CH$_2$—CH$_2$Cl or $R^{10}$ may represent H and CH$_2$—CH$_2$Cl—;

$R^8$ and $R^9$ together are —CH$_2$—CH$_2$— and $R^{11}$ and $R^{12}$ together are —CH$_2$—CH$_2$— and, if Y=S, X=N and n=2, $R^{11}$ and $R^{12}$ represent —CH$_2$—CH$_2$—, —CH$_2$—CH$_2$—O—CH$_2$—CH$_2$—or

—CH$_2$—CH$_2$—N—CH$_2$—CH$_2$—;
|
CH$_3$ or if
Y=O, X=N, n=1, $R^{12}$ is

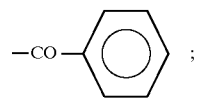

if
Y=O, X=N, n=2, $R^{11}$ and $R^{12}$ is

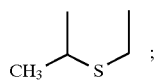

and, if
Y=O, X=O, n=1,
$R^8$ and $R^9$ are each —CH$_2$—CH$_2$—Cl, $R^{10}$ is H and $R^{11}$ and $R^{12}$ are —CH$_2$—CH$_2$— or —CH$_2$—CH$_2$—CH$_2$—.

2. A method according to claim 1, wherein the phosphorous derivative of alkaloids is an alkaloid derivative of thiophosphoric acid of the formula

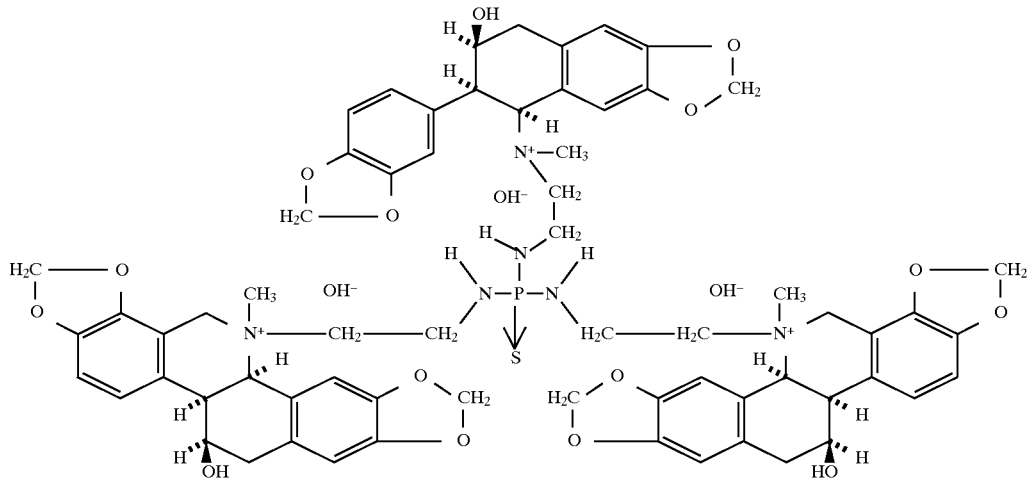
3. A method according to claim 1 wherein the reaction product of the alkaloids of chelidonium majus L. with thiophosphoric acid triaziridide is used.
* * * * *